United States Patent [19]
Tracy et al.

[11] Patent Number: 5,847,821
[45] Date of Patent: Dec. 8, 1998

[54] USE OF FIDUCIAL MARKS FOR IMPROVED BLANK WAFER DEFECT REVIEW

[75] Inventors: Bryan Mitchell Tracy, Oakland; Donald L. Wollesen, Saratoga, both of Calif.

[73] Assignee: Advanced Micro Devices, Inc., Sunnyvale, Calif.

[21] Appl. No.: 890,891

[22] Filed: Jul. 10, 1997

[51] Int. Cl.$^6$ ..................................................... G01N 21/00
[52] U.S. Cl. ............................................................ 356/237
[58] Field of Search ..................................... 356/237, 394

[56] References Cited

U.S. PATENT DOCUMENTS

| | | | |
|---|---|---|---|
| 5,479,252 | 12/1995 | Worster et al. | 356/237 |
| 5,640,236 | 6/1997 | Nagashima | 356/237 |

OTHER PUBLICATIONS

"Optimization of Wafer Surface Particle Position Map Prior to Viewing Wigh an Electron Microscope," by Man–Ping Cai, Yuri Uritsky, Patrick D. Kinney, American Institute of Physics, 1996, pp. 243–247.

*Primary Examiner*—Frank G. Font
*Assistant Examiner*—Amanda Merlino
*Attorney, Agent, or Firm*—H. Donald Nelson

[57] ABSTRACT

A method for navigating directly to defects on a blank wafer caused by particles dropped from process tools. A blank wafer is marked with fiducial marks, the number of initial defects on the blank wafer is determined and the position coordinates of the initial defects and the fiducial marks are recorded. The blank wafer is placed into a selected process tool and the additional defects that are caused by particles dropped from the process tool are detected in an inspection tool and their position coordinates are determined and recorded as well as the position coordinates of the fiducial marks. The blank wafer is then placed in an analysis tool that is able to navigate directly to each of the additional defects at a high magnification using the position coordinates of the fiducial marks.

8 Claims, 3 Drawing Sheets

USE OF FIDUCIAL MARKS FOR IMPROVED BLANK WAFER DEFECT REVIEW

BACKGROUND OF THE INVENTION

1. Field of the Invention

This invention relates generally to methods of defect analysis for semiconductor wafers. More specifically this invention relates to a method of defect analysis in which an analysis tool can navigate directly to previously identified defect locations at high magnification.

2. Discussion

In order to remain competitive, a semiconductor manufacturer must continuously increase the performance of the semiconductor integrated circuits being manufactured and at the same time, reduce the cost of the semiconductor integrated circuits. Part of the increase in performance and the reduction in cost of the semiconductor integrated circuits is accomplished by shrinking the device dimensions and by increasing the number of circuits per unit area on an integrated circuit chip. Another part of reducing the cost of a semiconductor chip is to increase the yield. As known in the semiconductor manufacturing art, the yield of chips (also known as die) from each wafer is not 100% because of defects caused during the manufacturing process. The number of good chips obtained from a wafer determines the yield. As can be appreciated, chips that must be discarded because of a defect increases the cost of the remaining usable chips.

A single semiconductor chip can require numerous processing steps such as oxidation, etching, metallization and wet chemical cleaning. Some of these processing steps involve placing the wafer on which the semiconductor chips are being manufactured into different tools during the manufacturing process. The optimization of each of these processing steps requires an understanding of a variety of chemical reactions and physical processes in order to produce high performance, high yield circuits. The ability to view and characterize the surface and interface layers of a semiconductor chip in terms of their morphology, chemical composition and distribution is an invaluable aid to those involved in research and development, process, problem solving, and failure analysis of integrated circuits. A major part of the analysis process is to determine if defects are caused by one of the process tools, and if so, which tool caused the defects.

As the wafer is placed into different tools during manufacture, each of the tools can produce different types of particles that drop onto the wafer and cause defects that have the potential to decrease the yield. In order to develop high yield semiconductor processes and to improve existing ones, it is important to identify the sources of the various particles that cause defects and then to prevent the tools from dropping these particles onto the wafer while the wafers are in the tools.

One approach used to identify the source of the particles is to analyze the particles as they lie on the wafer surface. A number of particle detectors have been developed to measure the number, location, and the size of the particles on the wafer surface. One type of particle detector is known as the laser surface particle detector (LSPD). However, the information provided by the LSPD, by itself, is sometimes not sufficient for identifying the source of the particles. In almost all cases, the particle must be further analyzed to identify what type of particle it is to assist in the determination of the source of the particle. A scanning electron microscope (SEM) equipped with an energy dispersive x-ray spectroscopy (EDS) system works well for measuring the morphology and chemical composition of particles. However, it is nearly impossible to find particles with a SEM on a relatively clean wafer surface. A technique was developed that uses a combination of the LSPD to locate particles on the wafer surface and the SEM/EDS system to analyze the particles. One of the combined systems is known as the Particle Analysis System (PAS) and this system and similar systems are used throughout the semiconductor industry. The PAS has been effective in identifying most particle contamination problems. However, as chip technology improves and device geometry shrinks, particles that can cause defects are also smaller. This requires that the analysis system be able to detect and analyze smaller particles. The major problem in the analysis of small particles with a PAS or similar system is the problem of finding the particles with the SEM after they have been identified by the LSPD. The limiting factor is the positioning accuracy of the LSPD, which may be insufficient to allow the SEM to use the minimum magnification to see the particles. The current industry standard is that a minimum of 1500× magnification is usually required on the SEM in order to see a 0.16 micron particle. For a typical CRT screen, this magnification translates to a field of view of 70×70 microns. This means that a particle's position must be known with an error less than 35 to 40 microns in order for the SEM to find the particle. As the position error increases, analysis time is wasted searching for particles. When the position error exceeds 100 microns an inordinate amount of time must be taken searching for particles.

A representative PAS system includes a Tencor 6200 LSPD and a JEOL 848 SEM equipped with a Kevex EDS. Typically, in such systems, a PC (personal computer) is used for data transfer between the LSPD and the SEM and for the manipulation of the data. The LSPD detects particles using a light scattering technique. The wafer is loaded into the LSPD chamber and the laser is raster-scanned over the wafer surface while the wafer is moved orthogonally to the scan direction. When the laser intersects a particle, light is scattered by the particle onto a detector. The magnitude of the light scattering signal provides information about the particle size. The measurement of the particle's position is more complicated. The position of the laser is known as a function of time and the scattering events produce a data file that contains the size and the x-y coordinates of each particle detected on the wafer surface. The wafer is then removed from the LSPD and loaded into a SEM. However, the coordinate system used by the x-y stage of the SEM is not the same as the coordinate system used by the LSPD. As a result, the wafer's orientation in the LSPD coordinate system differs from the wafer's orientation in the SEM's coordinate system. The PC must be able to transform the coordinate system used by the LSPD to the coordinate system used by the SEM.

To optimize the performance of PAS systems, it is necessary to improve the accuracy of particle position maps by reducing the targeting error. The targeting error is defined as the difference between particle positions predicted by the LSPD and the particle positions observed on the x-y stage. The source of nearly all the targeting error is caused by uncertainties in the LSPD particle map. A typical LSPD measures particle position with a resolution that exists as a rectangular region of 10 microns by 26 microns, however, this position is referenced to a less-accurately determined coordinate system. The coordinate system is aligned to the wafer in a specific orientation with respect to the wafer's center and notch positions. These positions are determined using a lower resolution (26 microns by 120 microns) measurement of the wafer's edge geometry. Ideally the alignment is insensitive to the wafer's orientation during scanning. From the uncertainties produced by resolution limits, it is expected that the LSPD will provide a relatively accurate particle position map, but one that is referenced to a significantly mis-aligned coordinate system. Therefore, a key step in the prior art in reducing the targeting error is to eliminate coordinate system misalignment. Another method in the prior art for reducing targeting error involves averaging multiple particle positions maps to reduce the influence of random uncertainties.

The first step in reducing targeting error involves fine tuning the coordinate transformation required to transfer the particle map from the LSPD frame to the SEM frame. The coordinate transformation is conducted in a multiple step process. A first-order transformation is accomplished by measuring the orientation of the wafer in the SEM coordinate system, and transforming the LSPD map data to reflect the same wafer orientation. The targeting errors are large, apparently due to errors in alignment of the LSPD coordinate system to the wafer. This alignment error can be substantially eliminated once several particles, termed reference particles, are located by the SEM. By comparing the coordinates of two particles in the SEM and LSPD frames, a second-order coordinate transformation can be made that effectively eliminates the influence of LSPD coordinate system alignment uncertainties. Further improvements in accuracy can be obtained by using more than two reference particles and averaging the coordinate transformation parameters.

Reduced targeting error is observed when two or more LSPD maps of the same set of particles are averaged. If two independent measurements of the same position are averaged, the random uncertainty associated with the average value should be less than the random uncertainty associated with the individual measurements. The main source of random errors is the limited resolution of the LSPD position measurement. However, if a wafer is scanned repeatedly without disturbing its position inside the LSPD chamber, the position measurements become extremely repeatable and averaging does not provide any benefit. If the wafer is removed from the chamber between scans, significant variability in position measurements is observed. Part of the variability is due to coordinate system misalignment, but when this factor is eliminated with a second-order transformation, variability is still observed in the particle positions. The map averaging technique takes advantage of this apparently random variability. The first and second-order targeting errors drop significantly when averaged scans are used. However, the improvement depends upon being able to find the reference particles. If two or more large, easily detectable particles are not present, it is extremely difficult and time consuming to use the above methods because of the difficulty of locating small particles.

In order to improve the yield it is necessary to reduce defects caused by specific tools. Such a tool might be an etcher or a metal deposition machine. The defects generated by such tools are commonly sampled on a "per wafer pass" basis using an unpatterned blank test wafer that is then inspected using standard inspection tools such as the KLA 255x, the Tencor 6200, and the Inspex 8500. The inspection tool generates defect size histograms and defect wafer maps. However, the inspection tool does not generate chemical information that might assist in identifying the source of the particle. The identification of the source of the particle is critical because the corrective action for a Teflon particle would be much different than the corrective action for a stainless steel particle. In order to obtain such chemical information, the particles must be individually subjected to some type of small area analysis such as an analysis using a full-wafer scanning electron microscope that uses energy dispersive x-ray spectroscopy (EDS) or some other chemical analysis method such as the whole-wafer Auger spectroscopy.

In order to obtain information from individual specific tools, blank test wafers are used for the particle check procedure. Because blank wafers are used, there are no lithography alignment points that can be used to remove wafer de-skew when the wafer is moved from one tool to another. As discussed above, the goal of the alignment procedure is to overlap the cartesian coordinate system of the inspection tool with the coordinate system of the defect review SEM. Commercially available software is available to make such alignment correction from Kinetek Corporation, Bothell, Wash. However, this software relies on being able to "blind navigate" to at least two defects on the wafer in order to make de-skew calculations. However, this causes a "chicken or the egg" problem:

1. There is a need to locate two defects to make de-skew corrections; and
2. The two defects can't be found because de-skew corrections have not been made.

The problem occurs because the particles are often micron sized and of low contrast and are exceedingly difficult to locate since a minimum magnification of 500× is required. Because such a high magnification is required, the field of view of the microscope is so small that an inordinate amount of time is required to find each defect. Referring to FIGS. 1 & 2 the effects of a small misalignment is illustrated. A wafer 100 is shown with a flat portion 102 on the wafer for purposes of orientation. It is noted that a notch can also be used to denote orientation of the wafer. The triangle 104 indicates the wafer has been inserted into a particular tool with a "skew" or has been inserted rotated around the center of the wafer. The triangle 104 is shown enlarged in FIG. 2 and shows that if the wafer is rotated by as little as 0.1 degrees, a particle 100 mm from the center will have an error in position of 175 microns, calculated as follows:

$$\tan \text{ (skew angle)} = \text{opposite/adjacent},$$

therefore $$\tan 0.1 = x/100 \text{ mm} = 0.00175 => x = 0.175 \text{ mm} = 175 \text{ microns}.$$

Therefore, what is needed is a method of identifying the position on a wafer of particles dropped from a tool onto the wafer and for an analysis tool to be able to rapidly locate the particles for analysis.

SUMMARY OF THE INVENTION

The present invention is directed to a method for navigating directly to defects on a blank wafer at high magnification. The blank wafer is marked with at least two fiducial marks. The number and position of initial defects on the blank wafer are determined and the coordinates of the initial defects and the fiducial marks are recorded. The blank wafer is then placed in a process tool. The number and position of a first set of additional defects caused by the selected process tool is determined and the coordinates of the first set of additional defects are recorded. The blank wafer is placed in an analysis tool that rapidly performs de-skew calculations using the position coordinates of the fiducial marks and then navigates directly to the position of each of the first set of additional defects at high magnification.

An analysis of each of the first set of additional defects is accomplished in the analysis tool. The determination of the location of each of the first set of defects is accomplished in an inspection tool such as a laser surface particle detector.

The present invention is also directed to a method of defect analysis in which the blank wafer can be sent through a second selected process tool and a second set of additional defects is determined and analyzed.

The present invention is better understood upon consideration of the detailed description below, in conjunction with the accompanying drawings. As will become readily apparent to those skilled in the art from the following description, there is shown and described an embodiment of this invention simply by way of illustration of the best mode to carry out the invention. As will be realized, the invention is capable of other embodiments and its several details are capable of modifications in various obvious aspects, all without departing from the scope of the invention. Accordingly, the drawings and detailed description will be regarded as illustrative in nature and not as restrictive.

BRIEF DESCRIPTION OF THE DRAWINGS

The novel features believed characteristic of the invention are set forth in the appended claims. The invention itself, however, as well as a preferred mode of use, and further objects and advantages thereof, will best be understood by reference to the following detailed description of an illustrative embodiment when read in conjunction with the accompanying drawings, wherein:

DETAILED DESCRIPTION

Reference is now made in detail to a specific embodiment of the present invention that illustrates the best mode presently contemplated by the inventors for practicing the invention.

Figure 1:
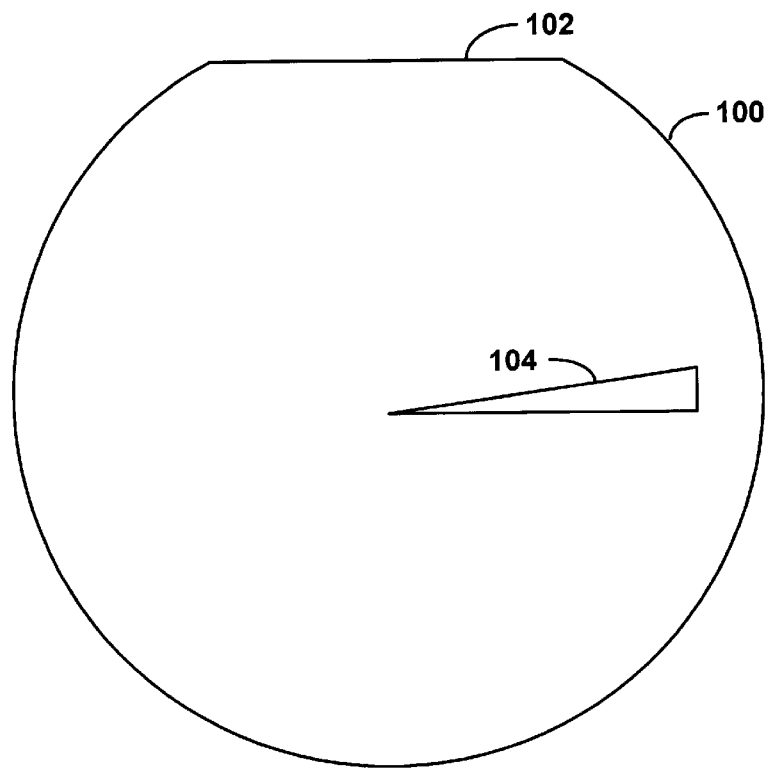
FIG. 1 shows a blank wafer with a flat area on the perimeter of the wafer used for orientation purposes.
Figure 2:
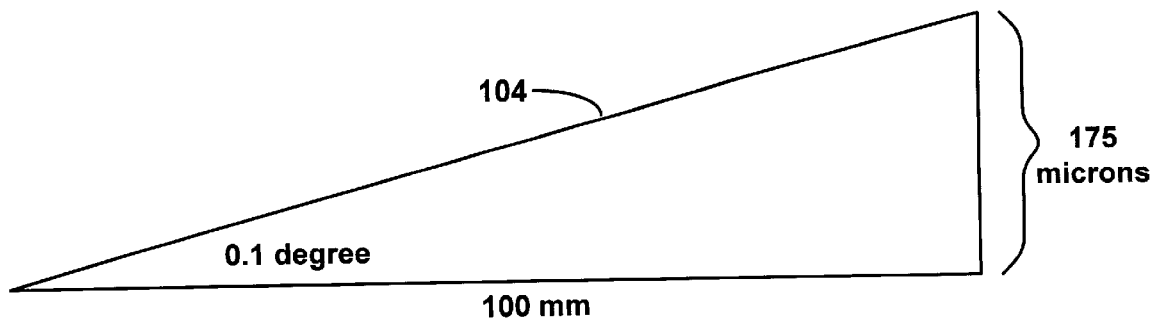
FIG. 2 is an enlarged diagram of an portion of the blank wafer shown in FIG. 1 to illustrate the amount position error introduced by rotation of the wafer in an analysis tool.

FIGS. 1 & 2 illustrates the effects of a small misalignment of a wafer 100 placed in an analysis tool. As is known in the semiconductor manufacturing art, the wafer 100 is marked in some way so that the orientation of the wafer can be determined as it is being transferred from one process tool to another. The wafer 100 in FIG. 1 is shown having a flat edge 102 on the perimeter. Other methods of determining the orientation of the wafer include notching the wafer. The triangle 104 in FIG. 1 represents the wafer being rotated (skewed) from its correct position after being transferred from one process tool to the next. The triangle 104 is shown enlarged in FIG. 2 and shows that if the wafer is rotated (skewed) by as little as 0.1 degree, a particle 100 mm from the center will have an error in position of 175 microns, calculated as follows:

tangent (skew angle)=position error/distance from center=tangent 0.1=position error/100 mm=0.00175=>position error=0.175 mm=175 microns.

Figure 3:
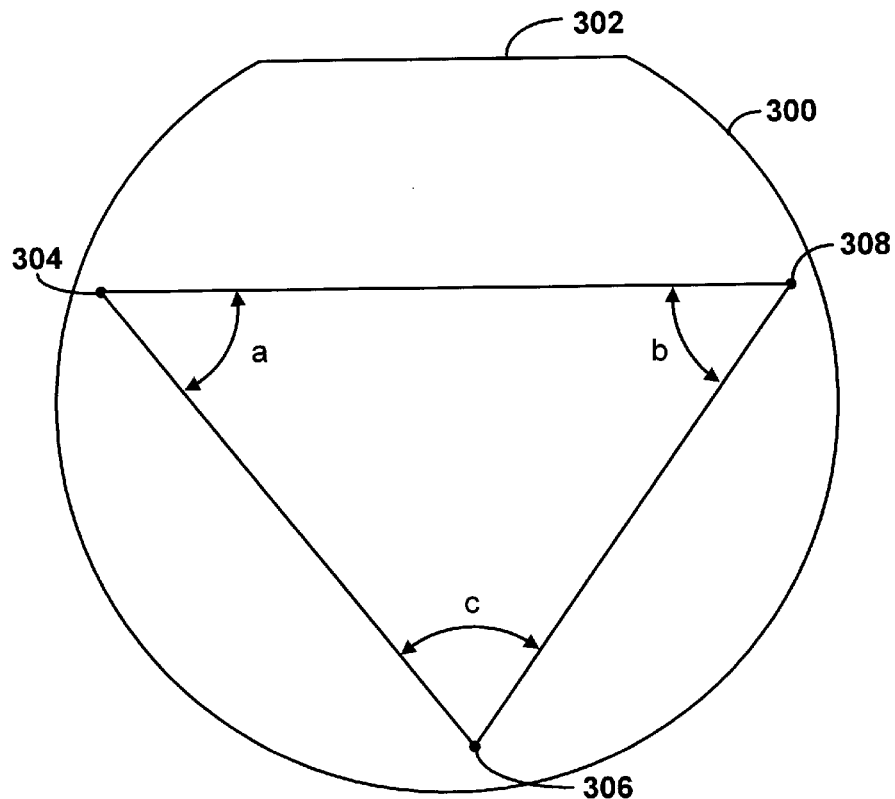
FIG. 3 shows a blank wafer with three fiducial marks inscribed thereon in accordance with the present invention.

FIG. 3 shows a blank wafer 300 with a flat edge 302 with three fiducial marks 304, 306, and 308 placed onto the surface of the wafer 300. The three fiducial marks 304, 306, and 308 are relatively large and easy to recognize marks and can be made by the laser marker or other scribing means that is used to scribe the run number and wafer number on each wafer at the beginning of the process flow. It should be understood that the description using three fiducial marks is not meant to be limiting and that comparable results can be obtained by using at least two fiducial marks. The marks are made on bare silicon and are typically exceptionally clean and free from debris. In addition, because they create topography, they are easily located by the scanning electron microscope (SEM). As can be appreciated, the placement of the fiducial marks is made to maximize the accuracy of de-skew calculations. The angles a, b, and c should be approximately 60 degrees to produce the most accurate results.

Figure 4:
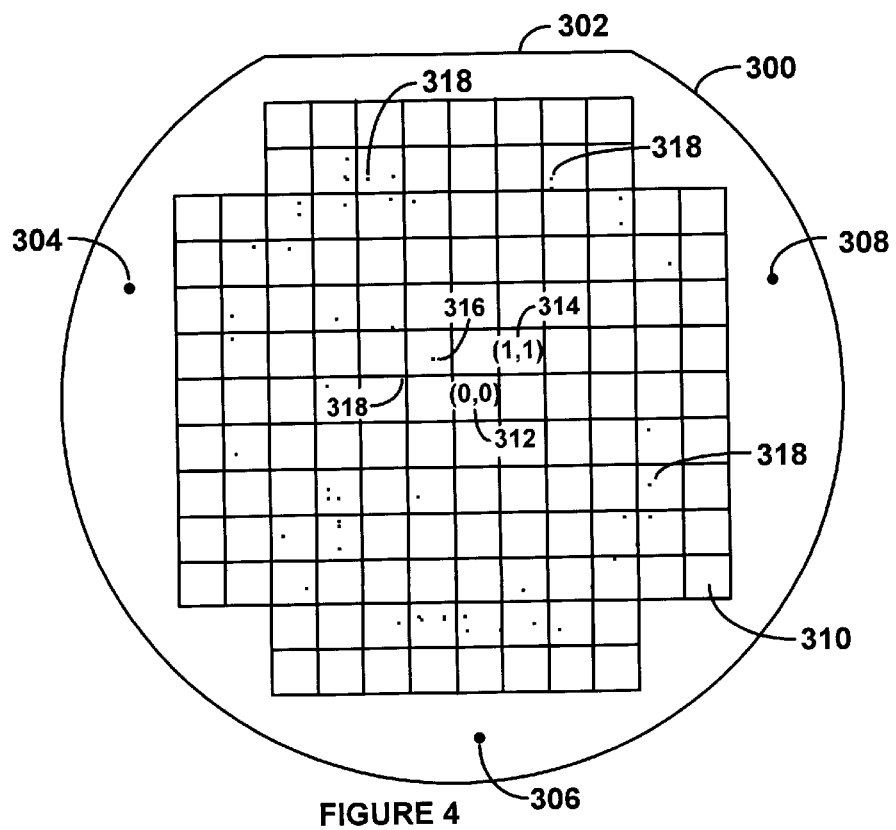
FIG. 4 shows chips as they would be manufactured on the wafer shown in FIG. 3 with particles distributed on the various chips and showing the three fiducial marks shown in FIG. 3.

FIG. 4 shows the wafer 300 with the outline of individual semiconductor chips, as they would be formed on the wafer 300. For example, the square labeled 310 would be an individual semiconductor chip. An example of a cartesian coordinate system that can be based, for example, on the outline of the chips is shown in FIG. 4. In this case, the center chip 312 would be termed the (0,0) chip. The chip that is one to the right and one up, labeled 314 would be the (1,1) chip. A defect position record is based upon the position of the defect in one of the labeled chips. For example, a typical defect record for a single defect would be as follows:

| Defect # | Die x | Die y | local x | local y | x size | y size | classification |
|---|---|---|---|---|---|---|---|
| 1 | −1 | 1 | 7845687 | 3089712 | 1181 | 1134 | 1 |

Referring to FIG. 4, the above record could be for the defect labeled 316 and the above values are defined as follows. The value for Die x (x coordinate) of −1 means that the die is one to the left of the die labeled (0,0) and the value for Die y (y coordinate) of 1 means that the die is one up from the die labeled (0,0). The local x and the local y values are measured from the lower left corner of the die. In this example, the local x is the horizontal distance from the lower left corner, indicated at 318, of the (−1,0) die and the local y is the vertical distance from the lower left corner 318 of the (−1,0) die. The x size is the size of the defect measured in the x direction and the y size is the size of the defect measured in the y direction. The classification is an arbitrary number assigned to various types of defects. For example, separate classification numbers can be assigned to a "flake," a "metal particle," a "Teflon particle," a "residue," a "glass flake," etc. It is to be understood that other position recordation schemes could be used. Also shown in FIG. 4 are a number of particles, such as the particle labeled 316 and other particles, generally indicated at 318, that have been "dropped" onto the surface of the wafer by individual process tools. As can be appreciated, the coordinates are loaded into a computer and various mathematical analyses can be performed, for example, an analysis to determine whether there is a "grouping" of a certain type of particle. Such an analysis may assist in the determination of the source of the particles.

Figure 5:
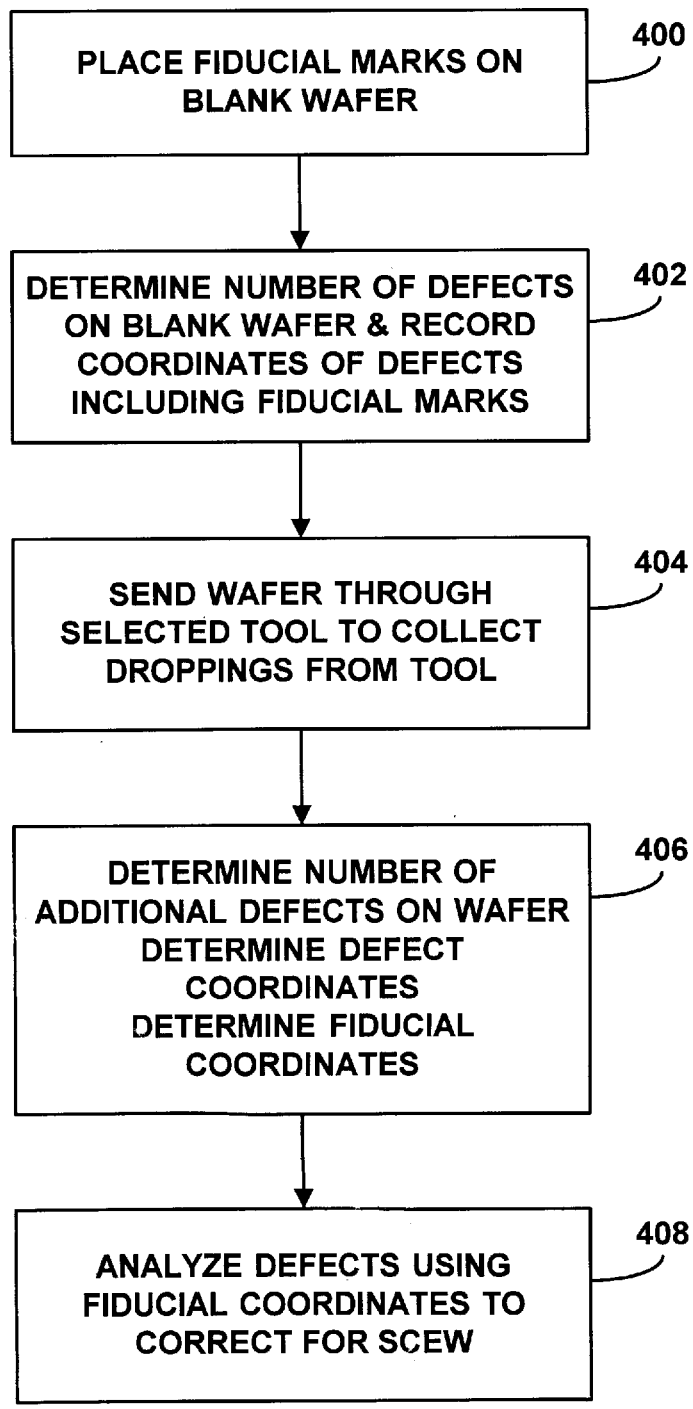
FIG. 5 is a flow diagram showing the process in accordance with the present invention.

FIG. 5 is a flow diagram showing the method of the present invention. The first step 400 is to place the fiducial marks on the blank wafer. The next step 402 is to determine the number of initial defects on the blank wafer. These initial defects are defects that are on the blank wafer when purchased. The positions of the initial defects are determined and recorded along with the positions of the fiducial marks on the blank wafer. The positions of the initial defects and fiducial marks are determined in an inspection instrument such as the laser surface particle detector. Standard inspection tools include the KLA 255x, the Tencor 6200, and the Inspex 8500.

The next step 404 is to send the blank wafer through a selected process tool which simulates an actual process step and in which the process tool may drop particles onto the blank wafer surface. The position, size, and chemical analysis of these particles may assist the process engineer in the determination of how to prevent the particles from being dropped onto the wafer and thus, to decrease the number of defects caused by the individual process tools.

The next step 406 is to place the wafer into the inspection tool to determine the location of the defects caused by the particular process tool. When the position coordinates of the additional defects are recorded along with the position coordinates of the fiducial marks, the wafer is then placed in an analysis tool, step 408, for some type of small area physical and/or chemical analysis. Typically, the particles are subjected to an analysis using a full-wafer scanning electron microscope that uses energy dispersive x-ray spectroscopy (EDS) or, alternatively, a method such as the whole-wafer Auger spectroscopy. In addition, there are other tools and methods available that can be used for the analysis of particles detected on chips. These other tools and methods include, but are not limited to, the following:

a. A focused ion beam (FIB) system that is used to selectively remove material on a submicron scale and make precise cross-sections on device features and/or structural defects;

b. Transmission electron microscopy (TEM) is a method that can be used to provide a detailed analysis of the smallest device feature and can be used to provide atomic resolution capability, for example, on the TOPCON 002B transmission electron microscope;

c. Atomic Force Microscopy (AFM) is a method that provides contact mode three dimensional topographic imaging of conductive and nonconductive surfaces from the atomic scale to micron scale under ambient condition and is used to determine surface micro-roughness measurements, surface texture and step height measurements;

d. Field Emission Scanning Electron Microscopy (FESEM) is a method that is applied, for example, with the JEOL 6400F field emission SEM with a Noran Light Element EDS System and is used for observing polished and FIB (focused ion beam) cross-sections as well as defect identification and analysis;

e. Ultra High Resolution Scanning Electron Microscopy (UHRSEM) is a method that is applied, for example, with the JEOL 6000F in-lens field emission SEM which is capable of observing high resolution surface topographical images and provides plan view examinations of defects or surface anomalies;

f. X-ray photoelectron spectroscopy (XPS)/electron spectroscopy for chemical analysis (ESCA) is a method that is applied, for example, with the VG ESCALAB 200 which is a multi-technique surface analysis system and provides information concerning the surface composition and chemistry;

g. Secondary ion mass spectroscopy (SIMS) is an analytical technique that can be used to provide elemental information and is commonly used to obtain depth profiles of implants and to investigate for low levels of contamination in deposited films;

h. Field emission Auger electron spectroscopy (FEAES) is a method that enables elemental and chemical analysis to be made and is applied to micron and sub-micron particle and defect analysis; and i. Fourier transform infrared spectroscopy (FTIR) is a technique that can be used to identify compound and is applied to identify compounds on the surface of the device.

The analysis tool is able to navigate directly to each of the additional defects with high magnification, using the position coordinates of the fiducial marks. The analysis tool uses the position coordinates of the fiducial marks to make de-skew calculations, orthogonality calculations, x-gain and y-gain calculations when the wafer is placed into an analysis or other tool. The de-skew calculations determine if the wafer has been rotated around its axis relative to the first tool in which measurements were taken. The orthogonality calculations ensure that the x-axis and y-axis, as measured, are 90 degrees apart. The x-gain and y-gain calculations ensure that the x-y coordinates measure the same distance when in different tools, for example, to correct for a different calibration in the second tool relative to the first tool. For example, the first tool may measure the x-distance between two points as 6 mm and the second tool may measure the same x-distance as 6.1 mm. The distance, as can be appreciated is fixed, the difference is how the alternate tools measured the distance. The analysis or other tool, using these calculations, can then navigate from one defect to the next using a magnification greater than or equal to 1000x.

The method of the present invention allows the wafer to be sent through a second process tool and the procedure repeated to allow an analysis of the "droppings" from the second process tool.

The foregoing description of the embodiments of the invention has been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What we claim is:

1. A method for analyzing defects on a wafer after manufacturing steps in at least two processing tools, the method comprising:

placing at least two fiducial marks on a wafer;

recording position coordinates of the at least two fiducial marks;

detecting initial defects on the wafer and recording position coordinates of the initial defects in relation to the position of the at least two fiducial marks;

placing the wafer in a first process tool;

detecting a first set of additional defects on the wafer caused by the first process tool and recording position coordinates of the first set of additional defects in relation to the at least two fiducial marks;

placing the wafer in an analysis tool;

performing de-skew calculations using the position coordinates of the at least two fiducial marks; and navigating directly to the recorded position of each of the first set of additional defects on the wafer at high magnification.

2. The method of claim 1, further comprising performing orthogonality calculations, x-gain and y-gain calculations using the position coordinates of the at least two fiducial marks.

3. The method of claim 2, further comprising performing an analysis of each of the first set of additional defects.

4. The method of claim 3, wherein detecting defects is accomplished in an inspection tool.

5. The method of claim 4, further comprising placing the blank wafer in a second process tool.

6. The method of claim 5, further comprising:

detecting a second set of additional defects on the wafer caused by the second process tool and recording position coordinates of the second set of additional defects in relation to the at least two fiducial marks;

placing the wafer in a second analysis tool;

performing de-skew calculations using the position coordinates of the at least two fiducial marks; and navigating directly to the position of each of the second set of additional defects on the wafer at high magnification.

7. The method of claim 6, further comprising performing, orthogonality calculations, x-gain and y-gain calculations using the position coordinates of the at least two fiducial marks.

8. The method of claim 7, further comprising performing an analysis of each of the second set of additional defects.

\* \* \* \* \*